(12) United States Patent
Jackson et al.

(10) Patent No.: US 6,525,808 B1
(45) Date of Patent: Feb. 25, 2003

(54) METHOD AND SYSTEM FOR LOCAL INDEX MEASUREMENT IN OPTICAL MATERIALS

(75) Inventors: Howard E. Jackson, Cincinnati, OH (US); Din Ping Tsai, Taichung (TW)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/454,281

(22) Filed: Dec. 3, 1999

Related U.S. Application Data

(60) Provisional application No. 60/110,914, filed on Dec. 4, 1998.

(51) Int. Cl.[7] ............................................... G01N 21/41
(52) U.S. Cl. ...................... 356/128; 356/132; 356/133; 356/135; 356/136; 250/234
(58) Field of Search .................... 356/128, 132, 356/133, 135, 136; 250/234

(56) References Cited

U.S. PATENT DOCUMENTS 5,994,691 A * 11/1999 Konada ...................... 250/234
6,173,604 B1 * 1/2001 Xiang et al. ................ 250/306

FOREIGN PATENT DOCUMENTS

DE 4244268 7/1994
GB 2323234 9/1998

* cited by examiner

Primary Examiner—Frank G. Font
Assistant Examiner—Roy M. Punnoose
(74) Attorney, Agent, or Firm—Dinsmore & Shohl LLP

(57) ABSTRACT

A method and system for determining a spatially local index of refraction in optical materials is provided. Light, including a near-field intensity, is collected above a surface of the material. A probe is oscillated at a plurality of frequencies and in a substantially perpendicular manner relative to the surface of the material to detect the near-field intensity of the light. A distance of the probe from the surface of the material is modulated. Based on a ratio of the near-field intensity of the light detected at the plurality of frequencies, the local index of refraction is determined.

20 Claims, 2 Drawing Sheets

METHOD AND SYSTEM FOR LOCAL INDEX MEASUREMENT IN OPTICAL MATERIALS

This application claims the benefit of U.S. Provisional Application No. 60/110,914, filed Dec. 4, 1998.

TECHNICAL FIELD

The present invention relates to methods and systems for measuring the local index of refraction in optical materials, and, for example, for measuring the local index of refraction in optical waveguide structures, and, more particularly, in one embodiment, to a method and system which uses a tuning fork to modulate the height of a probe in a near-field scanning optical microscope (NSOM), thereby allowing for measurement of the local index of refraction of optical materials and of integrated optics structures, including optical waveguide structures.

BACKGROUND OF THE INVENTION

In the field of microscopy, there is a growing need for higher spatial resolution. In the past, spatial resolution in optical microscopy and spectroscopy has been limited by diffraction. This diffraction limit is essentially dependent on the wavelength of the employed radiation. To get even higher spatial resolution, one has to go to the near-field regime.

Near-field scanning optical microscopy (NSOM), sometimes referred to as a scanning near-field optical microscopy (SNOM), avoids the diffraction limit by operating in the near field (i.e., in a spatial range much less than the wavelength of interest). In NSOM, an optical probe is generally used as a subwavelength-sized radiation source to emit light or as a subwavelength-sized aperture to collect light. An instrument utilizing NSOM can produce high-resolution optical imaging, characterization, and surface modification.

A typical NSOM optical probe comprises a tapered optical fiber coated with a thin metallic layer to create the aforementioned aperture. In order to operate this probe in the near-field, the scanning device must be able to actuate the probe in a controlled manner at distances over the surfaces of interest that are within the nanometer range. Moreover, a feedback system is typically implemented to keep the probe-to-sample distance constant. Keeping this distance constant operates to prevent probe and/or sample damage, as well as to ensure proper interpretation of the optical results.

In addition to providing near-field optical information, NSOM also provide simultaneous topographical images using atomic force microscopy (AFM) techniques. Conventionally, NSOM topographical images are produced using shear force feedback. In this mode, the fiber is attached to an actuator that oscillates the fiber end (i.e., the probe tip) near its resonance frequency and generally parallel to the surface of the sample. The probe is held in near-field distance of the sample by a feedback system, with the feedback also providing a topographical image of the sample.

More particularly, during the oscillation, as the probe approaches the sample's surface, forces between the tip and the sample result in the probe's oscillation amplitude being damped and creates a phase shift. This damping is a function of the distance between the sample surface and the probe tip. Thus, the interaction between the probe tip and the sample surface is used to keep the probe-to-sample distance constant.

Conventional optical systems are not capable of producing images of a sample's local indices of refraction. These and other methods average index of refraction measurements over part or all of the sample. Thus, there is a need to find methods and systems that measure local indices of refraction.

SUMMARY OF THE INVENTION

In one embodiment of the present invention, a method for determining a spatially local index of refraction in optical material is provided. Light, including a near-field intensity, is collected above a surface of the material. A probe is oscillated at a plurality of frequencies and in a substantially perpendicular manner relative to the surface of the material to detect the near-field intensity. A distance of the probe from the surface of the material is modulated. Based on a ratio of the near-field intensity of the light detected at the plurality of frequencies, the local index of refraction is determined.

In another embodiment of the present invention, a microscopy system is provided. The system includes a radiation source, a probe, an actuator, a modulator, and a processing module. The radiation source is configured to generate light in an optical material having a surface. The probe is configured to detect the near-field intensity of the light which is present just above the surface of the material. The actuator cooperates with the probe and is configured to oscillate the probe at a plurality of frequencies. The modulator cooperates with the probe and is configured to modulate a distance of the probe from the surface of the material. The processing module communicates with the probe and is configured to determine a local index of refraction of the material based on a ratio of the near-field intensity of the light detected at the plurality of frequencies.

Still other advantages and novel features of the present invention will become apparent to those skilled in the art from the following detailed description, which is simply by way of illustration various modes contemplated for carrying out the invention. As will be realized, the invention is capable of other different obvious aspects, all without departing from the invention. Accordingly, the drawings and descriptions are illustrative in nature and not restrictive.

BRIEF DESCRIPTION OF THE DRAWINGS

While the specification concludes with claims particularly pointing out and distinctly claiming the invention, it is believed that the same will be better understood from the following description taken in conjunction with the accompanying drawings.

The accompanying drawings, incorporated in and forming part of the specification, illustrate several aspects of the present invention and, together with their description, serve to explain the principles of the invention. In the drawings.

DETAILED DESCRIPTION OF THE PREFERRED EMBODIMENTS

Figure 1A:
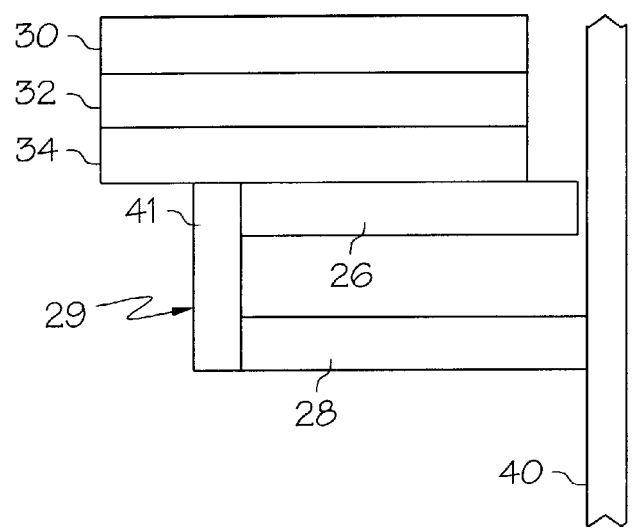
FIG. 1A is a side view of the system shown in FIG. 1.
Figure 1:
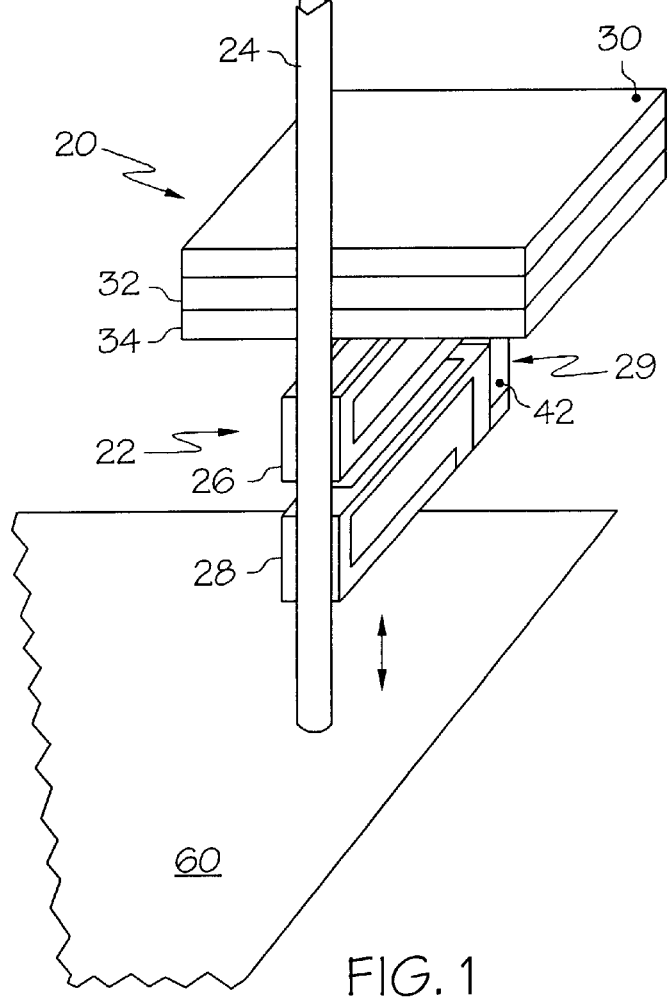
FIG. 1 is a perspective view illustrating an actuator, probe and modulator according to one embodiment of the present invention.
Figure 2:
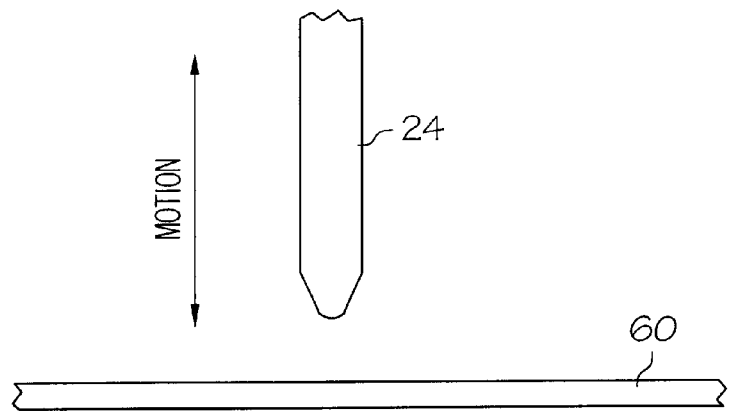
FIG. 2 is a side view of a probe tip in tapping mode according to one embodiment of the present invention.
Figure 3:
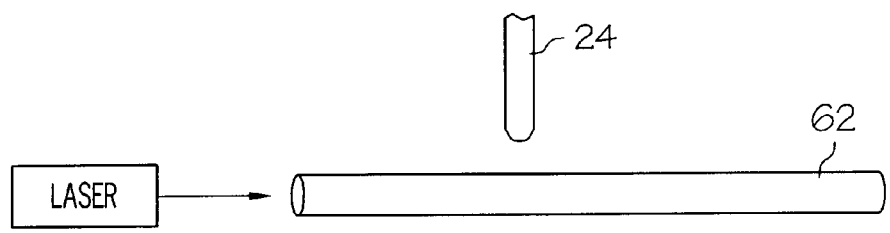
FIG. 3 is a side view depicting a system for measuring the local index of refraction in an optical material according to one embodiment of the present invention.
Figure 4:
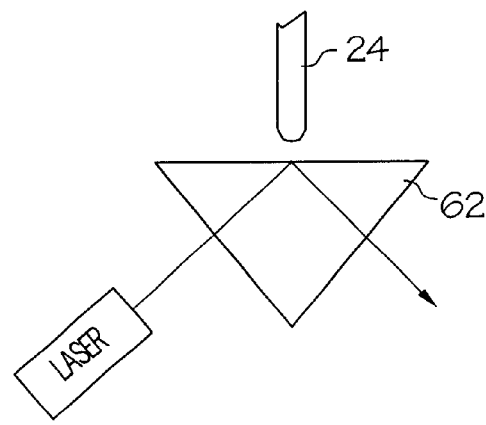
FIG. 4 is a side view depicting a system for measuring the local index of refraction in an optical material according to another embodiment of the present invention.

Referring now to the drawings in detail, wherein like numerals indicate the same elements throughout the views, FIG. 1 illustrates a preferred embodiment of the present invention. An actuator 20 is used to asymmetrically excite, for example, a near-field optical fiber probe 24, as a non-optical technique for probing the near-field. A modulator, preferably a tapping-mode tuning fork 22, is used to carry this mechanically asymmetric excitation to the probe 24. Probing a sample according to this invention is believed to generate better stability and sensitivity than in the shear force mode.

According to a preferred embodiment of the present invention, the actuator 20 comprises a piezoelectric material 30. This piezoelectric material 30 can be a piezoelectric plate. The piezoelectric plate is preferably a bimorph (e.g., a SNAVELEY PZT-5A series type bimorph having the following approximate dimensions: 0.25"×0.25"×0.021"). According to such an embodiment, the actuator 20 further preferably comprises a magnetic material 32 affixed to the piezoelectric plate 30, with the magnetic material preferably comprising a neodymium iron boron alloy (NdFeB) magnetic disk having a thickness of approximately 1.5 mm and a diameter of approximately 5 mm. In this embodiment of the present invention, the disk 32 can be glued under the piezoelectric plate 30. Ferromagnetic material 34, preferably an iron disk, can be affixed under the magnetic material 32.

As previously mentioned, tuning fork 22, having a pair of tines 26 and 28, a base 29, and a pair of electrodes 41 and 42, is also preferably provided. Upper tine 26 of tuning fork 22 is preferably fixed to ferromagnetic material 34. Tine 26 can be fixed to ferromagnetic material 34 by, for example, an adhesive, such as one comprising cyanoacrylate. According to a preferred embodiment of this invention, tines 26 and 28 of fork 22 should protrude approximately 3.5 mm from the edge of iron disk 32.

Probe 24 is preferably formed using a commercially available puller to pull an optical fiber 40. The pulled fiber 40 is subsequently coated with a thin layer of metal such as, for example, aluminum. The coating step is preferably done using a commercially available vacuum evaporator.

Probe 24 can, for example, be fixed on lower tine 28 (i.e., the opposite tine from the mechanically excited one) of tuning fork 22. Electrodes 41 and 42 of tuning fork 22 can be connected through a low-noise voltage preamplifier to a control unit. Preferably, the electrodes are connected through the preamplifier to the internal lock-in amplifier of an electronic control unit, such as, for example, a NANOSCOPE® IIIa system controller of a MULTIMODE™ scanning probe microscope ("SPM"), as sold by Digital Instruments of Santa Barbara, Calif.

According to the present invention, tuning fork 22 can be mechanically excited by actuator 20. When so excited, tuning fork 22 can represent a highly asymmetric system. This asymmetry can cause a voltage difference between electrodes 41 and 42 of the tuning fork under excitation, thus creating a signal for the control unit.

When actuator 20 oscillates or "taps" tuning fork 22 at or near the resonant frequency of the fork, the fork causes probe 24 to oscillate with an amplitude. When probe 24 is not in contact with or sufficiently near to the surface of a sample 60, the probe can oscillate with a high amplitude. As probe 24 nears the surface of sample 60, the amplitude of the oscillations is typically necessarily reduced due to, for example, energy loss from the interaction of the probe with various adhesion forces existing between the probe and the surface of the sample at close distances. These forces may include, for example, Van der Waals forces and capillary forces.

The aforementioned reduction in oscillation amplitude can be picked up at electrodes 41 and 42 of tuning fork 22 fixed to probe 24. The corresponding signal sent to the control unit by electrodes 41 and 42 can be used to adjust the probe-to-sample separation to maintain a constant amplitude of probe 24 oscillation. Preferably, a feed-back loop is used to control and maintain the oscillation amplitude.

The tapping-mode tuning fork according to a preferred embodiment of the present invention can provide excellent force sensing and feedback control characteristics. A NSOM equipped with one embodiment of the present invention can allow for simultaneous images of near-field optical information and AFM images of sample topography. Moreover, the "tapping" mode can inherently avoid problems associated with the shear force mode by providing sufficient amplitude to overcome the probe-sample adhesion forces, as well as avoiding pulling the surface of the sample sideways (as may sometimes occur with the application of shear force mode). Also, unlike contact modes, the potential damage of probe 24 and sample 60 from their necessitated contact can be reduced.

An additional feature of one embodiment according to the present invention is that the height of the oscillation of probe 24 can provide a novel means of making local optical index of refraction measurements. Through use of tuning fork 22, for example, the height of the oscillation of probe 24 can be modulated. As will be shown below, this can allow for directly measuring the local index of refraction of optical materials 62, such as an optical waveguide structure or optical materials undergoing total internal reflection (occurring where light attempts to move from a medium of a given index of refraction to a medium having a lower index of refraction).

According to such an embodiment of the present invention, the measured near-field light intensity I from an evanescent field above an optical material in which there is total internal reflection or above the surface of the optical waveguide, can be represented by Equation (1) below, where $I_o$ is the intensity at the surface, $I_s$ is the scattered background, and z is the probe height:

$$I=I_o e^{-2qz}+I_s \quad (1)$$

In Equation (1) above, q can be represented by the following equation, where k can be represented by $2\pi/\lambda$, and where $\lambda$ represents the wavelength of the light in the waveguide:

$$q=k(n_{eff}-1)^{1/2} \quad (2)$$

Moreover, in an embodiment where z is modulated, z can be represented by the following equation, where $z_o$ represents the initial height of the probe, and A and ω represent amplitude and frequency, respectively:

$$z=z_o+A\cos(\omega t) \quad (3)$$

Given the aforementioned relationships, I can thus be determined according to the Taylor series expansion shown in Equation (4) below:

$$I=I_o e^{-2qz_o}[1+q^2A^2-2qA\cos(\omega t)+q^2A^2\cos(2\omega t)-\ldots]+I_s \quad (4)$$

According to a preferred embodiment of the present invention, the ratio of the light intensity at different oscillation frequencies is measured. Although other ratios in the Taylor series expansion of Equation (4) could be considered, the light intensities at the 2ω and ω frequencies are preferably used. According to such an embodiment, this ratio can be detected using a commercially available lock-in amplifier.

When using the 2ω and ω frequencies, the ratio I(2ω) to I(ω) can be resolved to show a proportionality with the value of q, as expressed in Equation (5) below:

$$I(2\omega)/I(\omega)=(q^2A^2)/(-2qA)=-q(A/2) \quad (5)$$

Having determined this ratio, and after measuring the amplitude A, Equation (4) can be solved for q. Given a known λ and the determined q, Equation (2) can be solved for the local index of refraction $n_{eff}$.

A tapping-mode tuning fork NSOM according to a preferred embodiment of this invention can provide highly sensitive force sensing for AFM and NSOM images, and can measure the local effective refractive index of optical materials and create an image from a collection of these measurements. According to one embodiment of the present invention, for instance, a spacial resolution of 25 nanometers can be achieved when an exciting wavelength of 500 nanometers is employed.

Having shown and described the preferred embodiments of the present invention, further adaptations of the invention described herein can be accomplished by appropriate modifications by one of ordinary skill in the art without departing from the scope of the present invention. Accordingly, the scope of the present invention should be considered in terms of the following claims and is understood not to be limited to the details of structure and operation shown and described in the specification and drawings.

We claim:

1. A method for determining a spatially local index of refraction in optical material comprising:
   a) collecting light comprising a near-field intensity above a surface of the material;
   b) oscillating a probe at a plurality of frequencies and in a substantially perpendicular manner relative to the surface of the material to detect the near-field intensity of the light;
   c) modulating a distance of the probe from the surface of the material; and
   d) based on a ratio of the near-field intensity of the light detected at the plurality of frequencies, determining the local index of refraction.

2. The method according to claim 1, wherein the step of collecting light comprises coupling the light into the material wherein an evanescent field is formed above the surface of the material, the near field intensity being that of the evanescent field.

3. The method according to claim 2, wherein the step of coupling the light comprises coupling the light into the material with a laser.

4. The method according to claim 1, wherein the step of oscillating a probe comprises oscillating the probe at a first and a second frequency, the second frequency being twice that of the first frequency.

5. The method according to claim 1, wherein the step of oscillating a probe comprises asymmetrically exciting the probe.

6. The method according to claim 5, wherein the step of asymmetrically exciting the probe comprises mechanically asymmetrically exciting the probe.

7. The method according to claim 6, further comprising using a tuning fork to carry the mechanically asymmetric excitation to the probe.

8. The method according to claim 1, further comprising the step of detecting the ratio with a lock-in amplifier.

9. The method according to claim 1, further comprising the step of measuring an amplitude of the oscillation, wherein the step of determining the local index of refraction is based on the ratio and the amplitude.

10. A microscopy system, comprising:
    a) a radiation source configured to generate light in an optical material having a surface, a near-field intensity of the light being above said surface of the material;
    b) a probe configured to detect the near-field intensity of the light above the surface;
    c) an actuator cooperating with the probe and configured to oscillate the probe at a plurality of frequencies;
    d) a modulator cooperating with the probe and configured to modulate a distance of the probe from the surface of the material; and
    e) a processing module in communication with the probe and configured to determine a local index of refraction based on a ratio of the near-field intensity of the light detected at the plurality of frequencies.

11. The microscopy system according to claim 10, wherein the radiation source is configured to generate light having a wavelength of approximately 500 nanometers.

12. The microscopy system according to claim 10, wherein the radiation source comprises a laser.

13. The microscopy system according to claim 10, wherein the probe comprises an optical probe.

14. The microscopy system according to claim 13, wherein the optical probe comprises a near-field optical fiber probe.

15. The microscopy system according to claim 10, wherein the actuator comprises piezoelectric material.

16. The microscopy system according to claim 15, wherein the actuator further comprises magnetic material affixed to the piezoelectric material.

17. The microscopy system according to claim 16, wherein the actuator further comprises ferromagnetic material affixed to the magnetic material.

18. The microscopy system according to claim 10, wherein the modulator comprises a tuning fork.

19. The microscopy system according to claim 18, wherein the tuning fork comprises a tapping-mode tuning fork.

20. A microscopy system, comprising:
    a) means for generating light in an optical material having a surface, a near-field intensity of the light being above the surface of the material;
    b) means for detecting the near-field intensity of the light;
    c) means for oscillating the means for detecting at a plurality of frequencies;
    d) means for modulating a distance of the means for detecting from the surface of the material; and
    e) means for determining a local index of refraction based on a ratio of the near-field intensity of the light detected at the plurality of frequencies.

* * * * *